United States Patent [19]

Tsuchida

[11] Patent Number: 4,929,089

[45] Date of Patent: May 29, 1990

[54] APPARATUS FOR MEASURING TEMPERATURES INDICATIVE OF THERMAL CONDUCTIVITY

[75] Inventor: Yoshiki Tsuchida, Tokyo, Japan

[73] Assignee: Ishikawajima-Harima Heavy Industries Co., Tokyo, Japan

[21] Appl. No.: 298,052

[22] Filed: Jan. 18, 1989

[30] Foreign Application Priority Data

| Jan. 18, 1988 | [JP] | Japan | 63-4310 |
| Jan. 18, 1988 | [JP] | Japan | 63-7803 |
| Jan. 18, 1988 | [JP] | Japan | 63-7804 |
| Jan. 28, 1988 | [JP] | Japan | 63-18172 |
| Feb. 19, 1988 | [JP] | Japan | 63-21100 |
| Feb. 19, 1988 | [JP] | Japan | 63-21101 |

[51] Int. Cl.$^5$ .................. G01K 17/00; G01N 25/18
[52] U.S. Cl. .................. 374/44; 165/168; 374/29
[58] Field of Search .................. 374/29, 44, 43

[56] References Cited

U.S. PATENT DOCUMENTS

| 2,214,344 | 9/1940 | Paul | 165/170 X |
| 2,690,653 | 10/1954 | Kleist | 165/170 X |
| 3,279,239 | 10/1966 | Arends et al. | 374/44 |
| 4,553,852 | 11/1985 | Derderian et al. | 374/43 X |
| 4,630,938 | 12/1986 | Palczewska et al. | 374/43 X |
| 4,812,050 | 3/1989 | Epstein et al. | 374/29 X |

OTHER PUBLICATIONS

Annual Book of ASTM Standards, vol. 14.01, 1987, pp. 1–16.

Primary Examiner—Daniel M. Yasich
Attorney, Agent, or Firm—Oblon, Spivak, McClelland, Maier & Neustadt

[57] ABSTRACT

There is provided by the present invention an apparatus for measuring thermal conductivity. The apparatus is mainly composed of (a) a container adiabatically enclosing an inner space, (b) a heat source for heating a first surface of a specimen to be placed to divide the inner surface into a first space and a second space; (c) a first thermometer to measure the temperature of the first surface of the specimen; (d) a heat-flow-measuring means disposed in contact with the second surface of the specimen, for maintaining the temperature of the second surface of the specimen at a predetermined temperature and for measuring the thermal energy flowing through the second surface; and (e) a second thermometer for measuring the temperature of the second surface of the specimen. The apparatus realizes a stationary heat flow through the specimen from the first surface and the second surface thereof, and measures the temperature of the first and the second surface of the specimen and the thermal energy flowing through the specimen.

15 Claims, 12 Drawing Sheets

FIG.11
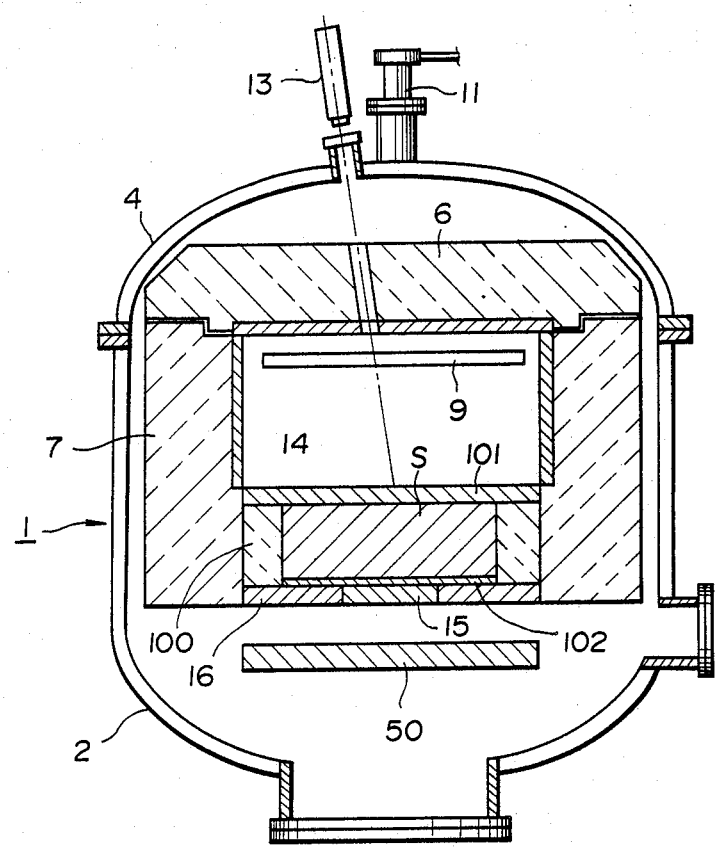
FIG.10   FIG.12
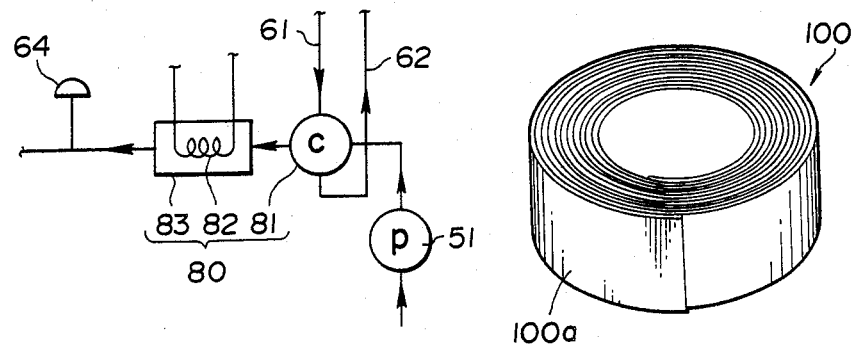

FIG.13
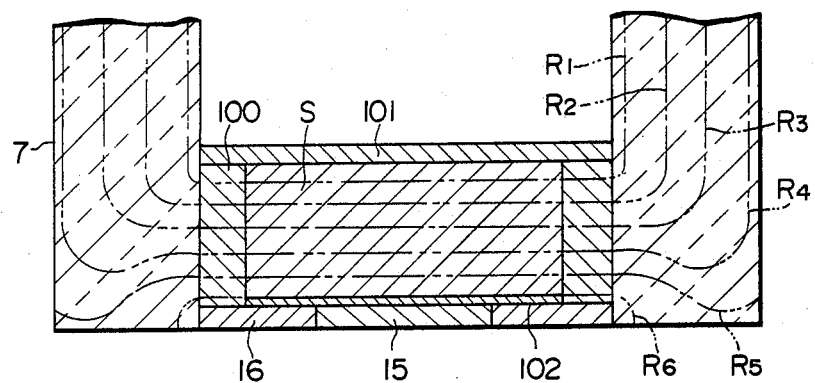
FIG.14 (a)   FIG.14 (b)
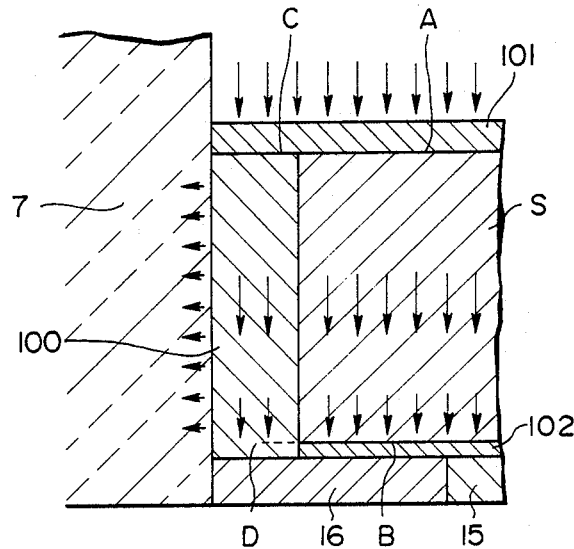 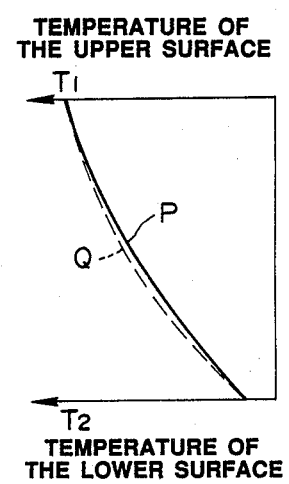

APPARATUS FOR MEASURING TEMPERATURES INDICATIVE OF THERMAL CONDUCTIVITY

BACKGROUND OF THE INVENTION

1. Field of the Invention

The present invention concerns an apparatus for measuring thermal conductivity used for measuring the thermal conductivity of various materials including thermal insulating and heat reserving materials etc, at a steadystate heat flux.

2. Prior Art

Generally the thermal conductivity of various materials used as thermal insulating and heat reserving materials is not steady but varies according to their temperature. Their thermal conductivity increases with the rise in their temperature, i.e. it becomes easy for them to conduct heat. This means that if the thermal conductivity of a material which is used at temperatures exceeding 1,000° C. is to be determined, then the measurement of its thermal conductivity must be done by actually heating it up to its service temperature.

A conventional method for measurement of thermal conductivity is prescribed in ASTM c-177-84 etc., and for example, it is shown in FIG. 18. This conventional apparatus for measuring thermal conductivity is equipped with a main heater b and an auxiliary heater c arranged respectively in the upper and lower parts of a thermally-insulated enclosure a, which heaters produce a steady downward heat flow in the enclosure a, and with a heat flow meter d placed in the upper part of the auxiliary heater c, which plate is designed for the measurement of heat flow quantity of the said steady heat flow.

Generally a device is used whose heat flow meter d contains a gas flow path of a spiral form through which passes the heat-measuring gas. By letting a specified volume of heat-measuring gas heated up to a specified temperature flow through the flow path, the amount of heat received is calculated from the temperature rise and flow rate of the heat-measuring gas.

In the conventional apparatus for measuring thermal conductivity made up as described above, a thermal equilibrium state is created in the enclosure a by means of the main heater b and the auxiliary heater c by arranging a specimen S whose thermal conductivity is to be measured at the center of the enclosure a and by arranging standard heat transfer plates $S_1$ and $S_2$ of known thermal conductivity above and below the specimen. The temperature gradient indicated as line B is thus formed through the specimen S and the standard heat transfer plates $S_1$ and $S_2$. The thermal conductivity of the specimen S at a particular temperature is calculated from the temperature difference measured by the thermometers $e_1$ and $e_2$ between the upper and lower surfaces of the specimen S in a steady state while maintaining the average inside temperature of the specimen S at the temperature to be measured, and from the amount of heat measured by the heat flow meter d at a steady heat flow, i.e. the amount of heat flow through the specimen S.

Hence, let the heat flow measured through the heat flow meter be Q (Kcal/h), the thermal conductivity of the specimen S be λ (Kcal/m.h.deg), the distance from the surface of the specimen S to the inner portion thereof be δ (m), the effective sectioned area of the specimen S be A ($m^2$) and the upper and lower surface temperatures be $\theta_1$ and $\theta_2$(°C.), then the following expression is obtained:

$$Q = (\lambda/t) \cdot A(\theta_1 - \theta_2)$$

From this equation thermal conductivity λ can be determined as follows:

$$\lambda = Q \cdot t / A(\theta_1 - \theta_2) \tag{1}$$

The standard heat transfer plates $S_1$ and $S_2$ serve not only to maintain the specimen S at a high temperature but also to verify and, if necessary, to correct the measured value by comparing the thermal conductivity determined from such surface temperatures and the above-mentioned amount of heat flow Q with the known thermal conductivity values for $S_1$ and $S_2$. The symbol g represents heaters for the compensation of wall temperature, which controls the surface temperature of the enclosure a so that the temperature gradient of the enclosure is consistent with the temperature gradient in the enclosure a in order to avoid the heat transfer between the enclosure a and its inner space thereby preventing the flow from dispersing from the peripheral surface of the enclosure a.

In the apparatus for measuring thermal conductivity as described above it goes without saying that obtaining an adequate accuracy of measurement requires the heat flow Q through the specimen S to be measured accurately. Consequently it is important to see to it that there is no dispersion of heat through the peripheral surface to the enclosure a, i.e. the heat flow occurs only downward and not sideward.

Although for this reason the above-mentioned conventional device is provided with heaters g for the compensation of the wall temperature, these heaters alone can not sufficiently prevent the heat in the specimen S and the standard heat transfer plates $S_1$ and $S_2$ from flowing sidewards when a testing temperature of the specimen S becomes higher (especially over 1500° C.). This results in an increase of errors in heat flow measurement.

According to the conventional apparatus, because the temperature is measured by means of thermocouples, the highest measurable temperature is limited to be relatively low.

SUMMARY OF THE INVENTION

The present invention which was made in view of the above facts has for its objective to provide a thermal-conductivity-measuring device capable of obtaining a sufficient accuracy of measurement.

The present invention concerns an apparatus for measuring thermal conductivity, consisting of:

(a) a container adiabatically enclosing an inner space, (b) a heat source for heating a first surface of a specimen;

(c) a first thermometer to measure the temperature of the first surface of the specimen;

(d) a heat-flow-measuring means disposed in contact with the second surface of the specimen, for maintaining the temperature of the second surface of the specimen at a predetermined temperature and for measuring the thermal energy flowing through the second surface; and (e) a second thermometer for measuring the temperature of the second surface of the specimen;

whereby realizing a stationary heat flow through the specimen from the first surface and the second surface thereof, and measuring the temperature of the first and the second surface of the specimen and the thermal energy flowing through the specimen.

BRIEF EXPLANATION ABOUT THE DRAWINGS

FIG. 4 (b) is a lateral section of the heat flow meter.

FIG. 5 (b) is a lateral section of the compensating cooling plate.

FIG. 10 is a drawing indicating another example of the circulating system.

FIG. 11 is a vertical section of the thermal-conductivity-measuring device in the third preferred embodiment of the present invention.

FIG. 12 is a perspective view indicating the enclosure in the device.

FIG. 13 is a partial vertical section of the device.

FIG. 14 (a) is a partial vertical section indicating a temperature distribution in the inner part of the device.

FIG. 14 (b) is a drawing indicating a temperature distribution in the specimen and in the heat-flow-compensation cylinder.

DETAILED DESCRIPTION OF THE INVENTION

In the following the second preferred embodiment of the invention is explained by reference to FIGS. 1 and 2.

Figure 1:
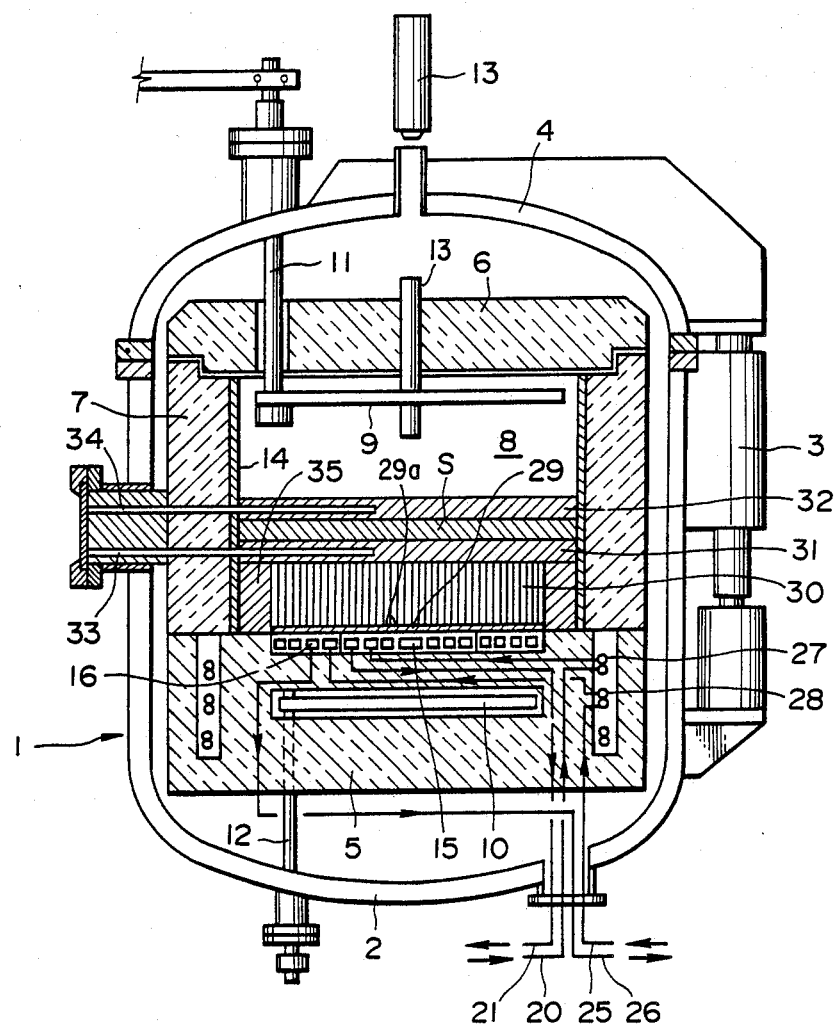
FIG. 1 is a vertical section of the thermal-conductivity-measuring device in the first preferred embodiment of the present invention.

FIG. 1 is a vertical drawing indicating the general configuration of the apparatus for measuring thermal conductivity in the case here in question. The numeral 1 indicates a housing made up of a body 2 with water jacket and of a cover 4 connected to the body 2 with a hinge 3.

In the housing 1 is built a measuring chamber 8 adiabatically enclosed by a container consisting of lower and upper disc shaped heat insulators 5 and 6 and a cylindrical lateral heat insulator 7 in which the specimen S is placed. In the upper space of this measuring chamber 8 is mounted a main heater 9 to maintain the measuring chamber 8 at a specified temperature while in the lower heat insulator 5 is embedded a compensating heater 10 to maintain the inside temperature of the lower heat insulator 5 at the same level as that of the heat flow meter (described later). To the main heater 9 and the compensating heater 10 are connected electrodes 11 and 12 which pass through the cover 4 of the housing 1 and the body 2. The numeral 13 indicates a radiation thermometer to measure the temperature in the measuring chamber 8.

The inside of the lateral heat insulator 7 which forms the side or peripheral wall of the measuring chamber 8 is covered with a wall-surface-temperature-compensating plate (called heat compensating plate hereinafter) 14 which is formed in a cylindrical shape with materials having an adequate resistance to heat and an excellent thermal conductivity like, for example, graphite, heat-resistant steel, molybdenum etc. This heat compensating plate 14, which is described later, transfers heat from the upper to the lower part of the measuring chamber 8 because of its excellent thermal conductivity and serves thus to maintain the inside temperature gradient of the lateral heat insulator 7 at the same level as that of the specimen S etc.

At the center in the upper part of the lower heat insulator 5 is arranged a disc shaped heat flow meter 15 around which an annular compensating cooling plate 16 is located.

Figure 4:
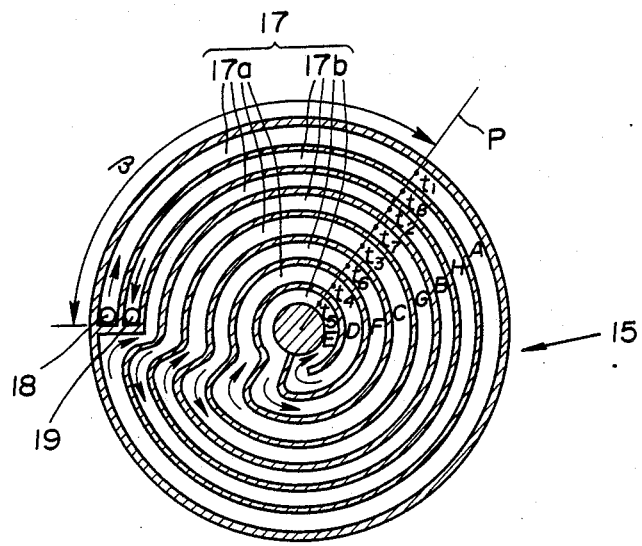
FIG. 4 (a) is a horizontal section of the heat flow meter in the said device.
Figure 4:
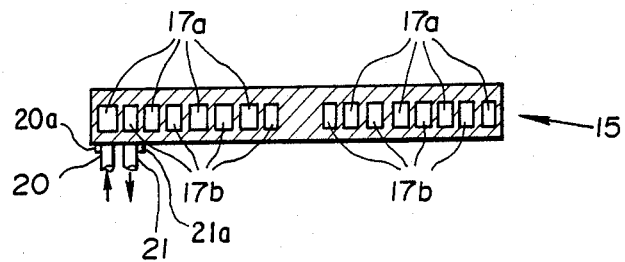

The heat flow meter 15, as shown in FIG. 4 (a) and (b), comprises a first measuring unit and contains a path 17 for heat-measuring gas for the measurement of the inner received heat, made up of upper and lower plates and a partition plate, each consisting of metal, which is formed like a double spiral with inlet-side and outlet-side paths adjacent to each other. An inlet 18 and an outlet 19 for heat-measuring gas are located side by side each at one end of the inlet-side path 17a and the outlet-side path 17b. The other ends of the said paths which are located at the center of the heat flow meter 15 are connected to each other. The heat-measuring gas introduced from the inlet 18 flows thus toward the center from the periphery in the inlet-side path 17a as indicated by an arrow in the drawing to be led at the center of the heat flow meter 15 toward the outlet-side path 17b through which it flows back to the periphery. To the above-mentioned inlet 18 and outlet 19 are connected an inlet pipe 20 and an outlet pipe 21, which together comprise a first fluid supplying means to lead the heat-measuring gas in and out as indicated by arrows in FIG. 1.

Figure 5:
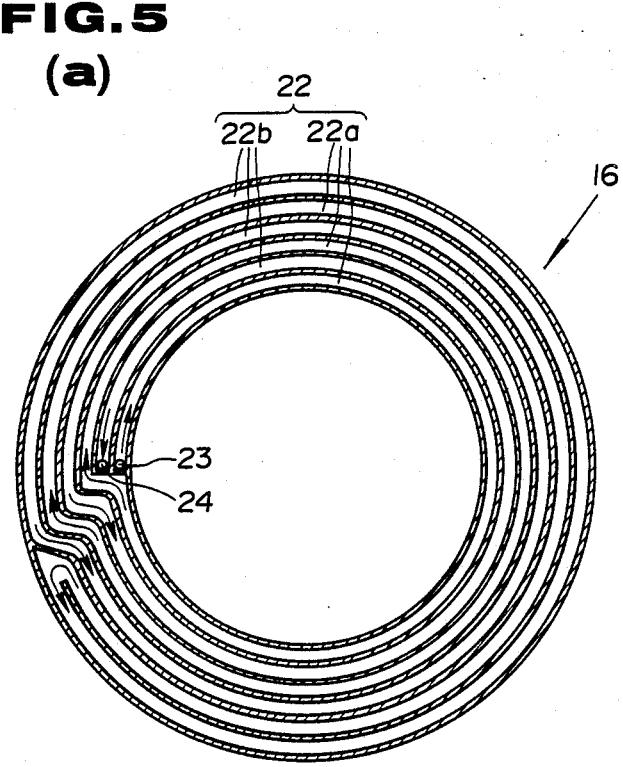
FIG. 5 (a) is a horizontal section of the compensating cooling plate in the said device.
Figure 5:
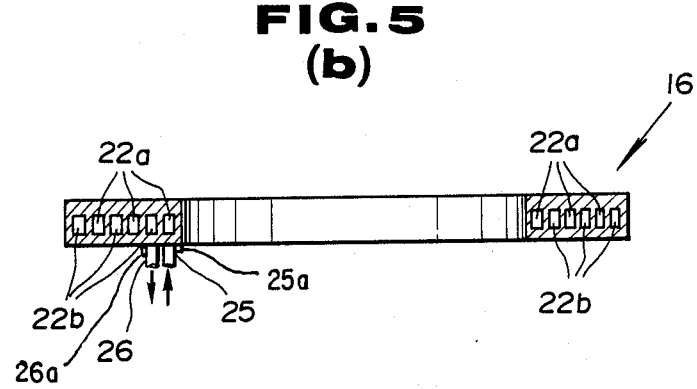
Figure 6:
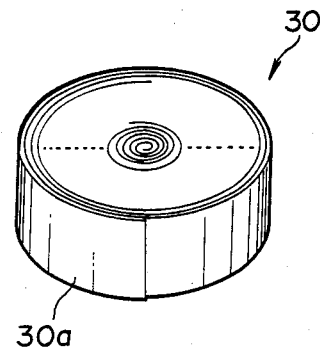
FIG. 6 is a perspective view of the standard heat transfer plate in the device.

The above-mentioned compensating cooling plate 16 comprises a second measuring unit and is built in the same way as the heat flow meter 15 except that it is annular and that the said heat flow meter 15 is placed at its center. That is to say, this compensating cooling plate 16, as indicated in FIG. 5 (a) and (b), contains a cooling gas flow path 22 formed with upper and lower plates and a partition plate, each consisting of metal, which is formed like a double spiral with inlet-side 22a and outlet-side 22b paths adjacent to each other. An inlet 23 and an outlet 24 for cooling gas are located side by side each at one end of inlet-side and outlet-side paths 22a and 22b located at the innermost periphery of this compensating cooling plate 16 while the other ends of the said paths which are located at the outermost periphery of the compensating cooling plate 16 are connected to each other. The cooling gas introduced from the inlet 23, as indicated by an arrow in the drawing, flows thus through the inlet-side path 22a from the inner to the outer periphery from where it is led to the outlet-side path 22b, then through the outlet-side path 22b back to the inner periphery and then out of the outlet 24 to the periphery. To the above-mentioned inlet 23 and outlet 24 are connected an inlet pipe 25 and an outlet pipe 26, which together comprise a second fluid supplying means to lead the cooling gas in and out as indicated by arrows in FIG. 1.

The above-mentioned heat-measuring and cooling gases are heated to a specified temperature by gas preheaters 27 and 28 (as shown in FIG. 1) embedded in the lower heat insulator 5 and are then led into the heat flow meter 15 and the compensating cooling plate 16, respectively. Thermometers are provided for measuring the temperature at the inlet 18 and outlet 19 for heat-measuring gas as well as at 25a and 26a for the inlet 23 and outlet 24 for cooling gas, respectively.

The above-mentioned heat flow meter 15, like the one used in the conventional apparatus for measuring thermal conductivity, (FIG. 18) is intended to measure the temperature at the inlet 18 and outlet 19 and thereby measure the received heat by the heat-measuring gas, i.e. the transmitted heat through the specimen S, on the basis of the temperature difference between the inlet 18 and the outlet 19 and the gas flow at the inlet and the outlet 19. The compensating cooling plate 16 placed around the periphery of the heat flow meter 15, on the other hand, is intended to prevent the outward flow of heat from the heat flow meter 15 by maintaining its temperature at the same level as the heat flow meter 15 and is intended to control the heat flow which flows from the measuring chamber 8 to the heat flow meter 15 to become lateral flow.

On top of the above-mentioned heat flow meter 15 and compensating cooling plate 16 is arranged a heat-measuring plate 29 on top of which is located a disc shaped standard heat transfer plate 30 of a material with a known thermal conductivity.

Figure 7:
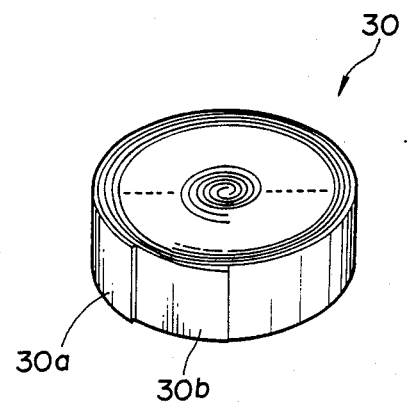
FIG. 7 is a perspective view indicating another example of the standard heat transfer plate.
Figure 18:
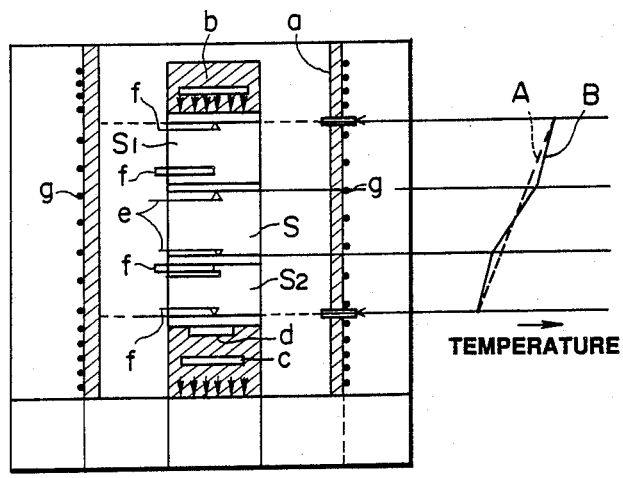
FIG. 18 is a vertical section indicating a case of a conventional apparatus for measuring thermal conductivity.

This standard heat transfer plate 30, which, like the abovementioned; standard heat transfer plates $s_1$ and $s_2$ used (FIG. 18) in the conventional device shown in FIG. 18, is intended to maintain the temperature of the specimen S at a high level and the surface temperature of the heat flow meter 15 at a low level and which is at the same time intended to verify and correct a measured heat flow value determined from the temperature difference and known thermal conductivity by measuring the upper and lower surface temperature of the heat transfer plate 30 with a thermometer 29a inserted in the heat-measuring plate 29 and a thermocouple 33 inserted in the lower heat-measuring plate described later, is a layer-built structure made of laminar heat insulator 30a such as formed plate of carbon fiber densely wound in a spiral form as shown in FIG. 7. As its laminar heat insulator 30a has a wound form, this standard heat transfer plate 30 has a thermal conductivity 2 to 3 times higher in the direction of thickness than in the direction of diameter. This means that this standard heat transfer plate 30 transfers heat easily in the direction of thickness but with difficulty in the direction of diameter.

On top of the standard heat transfer plate 30 is placed a lower heat-measuring plate 31 on which is placed the specimen S whose thermal conductivity is to be measured while an upper heat-temperature plate is placed on top of the said specimen S. Inserted in the lower. 31 and upper 32 heat-measuring plates are thermocouples 33 and 34 respectively which measure the temperature of the lower and upper surfaces of the specimen S.

The numeral 35 indicates a cylindrical heat insulator placed outside the standard heat transfer plate 30.

To measure the thermal conductivity $\lambda$ of the specimen S at a high temperature by means of the device set up as described above, first place the specimen S in the measuring chamber 8, put the upper measuring plate 32 onto the said specimen and insert the thermocouple 34 into the upper measuring plate 32. Seal up the measuring chamber 8 with the upper heat insulator 6, close the cover 4 of the housing 1, heat the measuring chamber 8 with the main and compensating heaters 9 and 10 up to a specified preset temperature to maintain the inner temperature of the specimen S at T° C. at which the thermal conductivity is to be measured. Also, heat the measuring and cooling gases with the preheaters 27 and 28 respectively up to a specified temperature and let them flow through the heat flow meter 15 and the compensating cooling plate 16 to maintain the temperatures of the gases at a level equal to each other.

When a stationary thermal equilibrium is reached in the temperature of the measuring chamber 8 as well as in the inner temperatures of the specimen S and the standard heat transfer plate 30, i.e. when no temperature change is observed, then measure the upper and lower surface temperatures $\theta_1$ and $\theta_2$ of the specimen S with the thermocouples 34 and 33 as well as the inlet and outlet temperatures of the measuring gas flowing through the heat flow meter 15 and find the received heat, i.e. the transmitted heat through the specimen S, on the basis of the temperature difference and the quantity of flow of the measuring gas, and determine the thermal conductivity $\lambda$ of the specimen S at a temperature of T with the above-mentioned equation (1) from the transmitted heat and the upper and lower surface temperatures $\theta_1$ and $\theta_2$ and the thickness t of the specimen S. In this case the effective area A of the specimen S equals the area of the heat flow meter.

Also, it suffices to determine the temperature difference between the upper and lower surfaces of the standard heat transfer plate 30, then determine the thermal conductivity from the said temperature difference and the above-mentioned transmitted heat Q and compare the heat transfer conductivity thus determined with the known one in order to verify and, if necessary, to correct the result of the measurement.

The apparatus for measuring thermal conductivity explained above in which the inside of the measuring chamber 8 is covered with the heat compensating plate 14 prevents a heat flow from the sides of the specimen S without installing wall-temperature-compensating heaters g required in the conventional thermal conductivity-measuring and as such can accurately measure the amount of heat conducted through the specimen S.

Even in this device like the conventional one it is impossible to avoid a heat radiation from the lateral heat insulator 7 due to a temperature difference with the outside. This would therefore result, if no particular measure is taken, in a decrease in the temperature of the lower portion of this lateral heat insulator 7, i.e. the temperature of the specimen S and the periphery of the standard heat transfer plate 30. The device here described in which the inside of the measuring chamber 8 is provided with the heat compensating plate 14 of a highly heat-conductive material extending therein, however, permits such an amount of heat as may be lost by the effect of heat conduction to be conducted through the heat compensating plate 14 to the lateral heat insulator 7 so that the heat radiation from the specimen S and the standard heat transfer plate 30 to their peripheries can be avoided effectively. As the function of the heat compensating plate 14 is to transmit heat downward therethrough to the peripheral part of the specimen, the heat compensating plate 14 may not be disposed to cover the whole part of the chamber 8 above the specimen. It is sufficient that the heat compensating plate 14 protrudes in the measuring chamber 8 from the peripheral part of the specimen.

Figure 2:
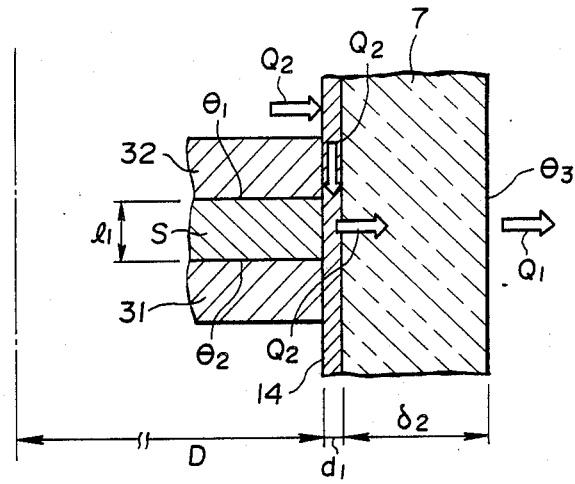
FIG. 2 is a drawing explaining about the effect of heat transfer of the wall-temperature-compensating plate in the said device.

The following gives a full account of the above-mentioned fact by reference to FIG. 2. Let the average thermal conductivity of the lateral heat insulator 7 be $\lambda_1$, the distance from the surface thereof be $\delta_2$, the inside diameter be D, the height of the specimen S be $l_1$, the temperature of the upper surface of the specimen S be $\theta_1$ and that of the lower surface be $\theta_2$ and the external surface temperature of the lateral heat insulator 7 be $\theta_3$, then the amount of heat lost $Q_1$ from the lateral heat insulator 7 in contact with the specimen S through the heat compensating plate 14 can be approximately expressed as follows (the following equation is an approximation obtained on the assumption that the diameter of the lateral heat insulator 7 is large enough to allow an approximation in the form of a heat transfer through a flat plate and that the distance $\delta_2$ from the surface of the heat compensating plate which is an extremely small value as compared with D is negligible):

$$Q_1 = (\lambda_1/\delta_2) \cdot \pi \cdot D \cdot l_1 \cdot [\{(\theta_1 + \theta_2)/2\} - \theta_3]$$

The upper part of the heat compensating plate 14 which faces the inside of the measuring chamber 8, on the other hand, has a sufficiently high temperature. Now, if this temperature decreases as a result of the above-mentioned heat loss from the lateral heat insulator, then this gives rise to an effective heat transfer from the upper to the lower part of the heat compensating plate 14, as indicated by an arrow in the drawing whereby heat is transferred from the upper space of the measuring chamber 8 through the heat compensating plate 14 to the lateral heat insulator 7. The transmitted heat thus transferred $Q_2$ can be approximately expressed as follows if we let the average thermal conductivity of the heat compensating plate 14 be $\lambda_2$ and the distance from the surface thereof be $\delta_1$:

$$Q_2 = \{\lambda_2/(l_2/2)\} \cdot \pi \cdot D \cdot d_1 \cdot \{(\theta_1 - \theta_2)/2\}$$

Therefore, by properly setting the values of the thermal conductivity $\lambda_2$ and the distance $\delta_1$ of the heat compensating plate 14, there will be no decrease in the temperature of the lateral heat insulator 7 nor therefore decrease in the temperature of the heat compensating plate 14 so that the temperature of the heat compensating plate 14 will naturally remain at the same level as that of the specimen S. As a result, the heat flowing through the specimen S can be prevented from flowing outward through the heat compensating plate 14 and the lateral heat insulator 7.

Although the above example of calculation concerns the outer periphery of the specimen S, there is also a similar lateral flow of heat at the outer periphery of the standard heat transfer plate 30. It therefore goes without saying that the actual distance $\delta_1$ of the heat compensating plate 14 is determined by making a calculation taking into account the whole range of possible lateral heat flows.

Since the device in the first preferred embodiment employs the heat flow meter 15 with the gas flow path 17 formed like a double spiral, the surface temperature of the heat flow meter never becomes uneven which makes it possible to obtain adequate accuracy of measurement.

This means that if in the above heat flow meter 15 we let the gas temperature at the inlet 18 be $t_0°$ C. and that at the outlet 19 be $t_0°$ C., we obtain the following equation because it is possible to maintain a nearly mean temperature of the said temperatures:

$$T = (t_o + t_e)/2$$

The following gives a full account of this fact by reference to FIG. 4. Let the paths from the outer periphery side of the inlet-side path of the above-mentioned heat flow meter 15 be marked in regular order with A, B, C and D and those from the center of the outlet-side path 17 be marked in regular order with E, F, G and H and let the gas temperatures in the respective paths A through H on the line P located at a rotation angle of B degrees from the inlet 18 and the outlet 19 be $t_1$ through $t_8$ and now examine the paths A and H, then since we can consider the radii of these paths A and H to be approximately equal to each other, the temperature $t_1$ on the line P in the path A may, if we let each of the said radii be R and the specific amount of gas temperature rise per unit length of the gas paths A and H be $\Delta t$, be expressed as follows because the amount of heat received by a measuring gas may be assumed to be proportional to the length of a gas path.

$$t_1 = (\beta/180) \cdot \pi \cdot R \cdot \Delta t + t_0$$

The temperature $t_8$ on the line P in the path H, on the other hand, may be expressed as follows:

$$t_8 = t_e - (\beta/180) \cdot \pi \cdot R \cdot \Delta t$$

Therefore, we obtain:

$$t1 - t8 = ti + to.$$

Hence, if we let the average temperature between the paths A and H on the line P be $T_{18}$, then we obtain:

$$T18 = (t1 + t8)/2 = (ti - to)/2.$$

Similarly the following equation holds:

$$t2 + t7 = t3 + t6 = e4 = t5 = ti + to,$$

hence, if we let the average gas temperature in the paths B and G be $T_{27}$, the one in paths C and F be $T_{36}$ and the one in paths D and E be $T_{45}$, then we obtain:

$$T27 = T36 = T45 = (ti + to)/2.$$

As can be from the above, in the heat flow meter 15 the average temperatures of the measuring gases passing through the paths which are adjacent to each other are all the same and hence the surface temperature of the heat flow meter, too, is the same so that ultimately the heat flow meter 15 as a whole has an almost even temperature.

In addition, the apparatus for measuring thermal conductivity here under review is provided with that annular compensating cooling plate 16 around the heat flow meter 15 which like the heat flow meter 15 also maintains an even temperature all over the surface. As a result, by controlling the temperature of cooling gas at the inlet 23 and the outlet 24 so as to make it equal to that of the measuring gas at the inlet 18 and the outlet 19, we can eliminate the flow of heat between the heat flow meter 15 and the compensating cooling plate 16. In this respect, too, we can improve the accuracy of measurement.

Besides, since in the device according to the first preferred embodiment the standard heat transfer plate 30 employed has a thermal conductivity which is small in the axial direction than in the radial direction due to the particular spiral form of the laminar heat insulator 30a, the steady transmitted heat through the specimen S flows only downward through the standard heat transfer plate 30 and is restricted from flowing sidewards. Consequently the loss of heat flowing sideward from the standard heat transfer plate 30 will naturally be minimized. In this respect, too, the apparatus for measuring thermal conductivity here under review is capable of exactly measuring the transmitted heat Q and hence improving the accuracy of measurement.

In the above-mentioned the first preferred embodiment it should be noted that although use is made of graphite, heat-resistant steel or molybdenum as a material for the heat compensating plate, it is quite possible, to use any other material as long as such material is heat-resistant enough to withstand use at high temperatures and is much more heat-conductive than the heat insulator in use.

Assumption is made on the other hand in the above-mentioned the first preferred embodiment that the heat lost from the lateral heat insulator 7 and the transmitted heat from the heat compensating plate 14 to the heat insulator 7 are both constant in the direction of thickness of the specimen S so that the thickness of the heat compensating plate 14 is assumed to be constant which in normal cases proves to be sufficiently effective. However, there is actually a temperature gradient developed in the specimen S so that the above-mentioned heat loss $Q_1$ and the transmitted heat $Q_2$ are not constant in the direction of thickness of the specimen S. Consequently, if we make the transmitted heat to all the parts of the lateral heat insulator 7 vary according to the amount lost by making the thickness of the heat compensating plate 14 gradually smaller from the upper to the lower part, then we can obtain a higher accuracy of measurement.

Figure 3:
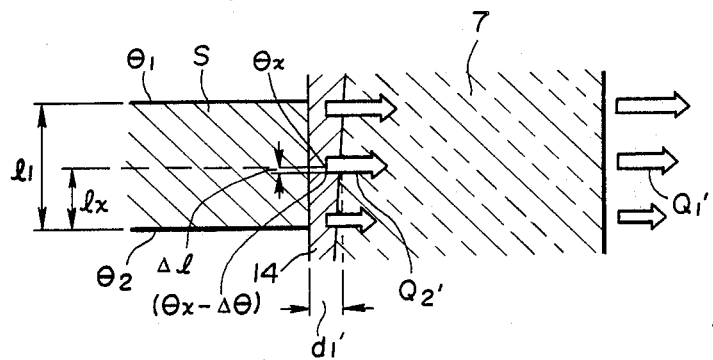
FIG. 3 is a drawing explaining about the effect of heat transfer obtained when the thickness of the wall-temperature-compensating plate is varied.

The following gives a full account of this fact by reference to FIG. 3. Consider the heat balance at a distance to $1_x$ from the lower part of the specimen S, as indicated in FIG. 3 and let the heat loss at this position $1_x$ from the lateral heat insulator 7 be $Q_1'$, then this $Q_1'$ may be approximately expressed as follows:

$$Q_1' = (\lambda_1/\delta_2) \cdot \pi \cdot D \cdot 1_x \cdot \{\theta_2 + (\theta_1 - \theta_2) \cdot 1_x/2 1_1 - \theta_3\}$$

Also, consider the heat balance in the heat compensating plate 14 at the above-mentioned position $1_x$ and assume an extremely small length $\Delta_1$ in this part, then the transmitted heat $Q_2'$ through this part $\Delta_1$ may, if we let the average heat conductivity of the heat compensating plate 14 be $\lambda_2$ and the distance from this place of the heat compensating plate 14 be $\delta_1'$, be approximately expressed as follows:

$$Q_2' = (\lambda_2/\Delta 1) \cdot \pi \cdot D \cdot d_1' \cdot \Delta \theta$$

where Th is the temperature difference between the inner temperature $\theta_x$ of the heat compensating plate 14 at the position $1_x$ and that of the same at the extremely small distance $\Delta_1$ from the position $1_x$. This temperature difference $\Delta \theta$ is a constant which is proportional to $\Delta_1$ in case the temperature gradient of the specimen S (i.e. degree of change between the upper $\theta_1$ and lower $\theta_2$ surface temperatures) is linear (all the examples of calculations hitherto introduced are such cases).

Consequently, by determining a distance $z_1'$ such that the above equations result in $Q_2' = Q_1'$, i.e. by providing such a change in the distance $z_1'$ as may be proportional to the value $Q_1'$, it becomes possible to cause the heat loss at each one the positions in the direction of thickness of the specimen S from the lateral heat insulator to be equal to the transmitted heat through the heat compensating plate 14. For this purpose it suffices to vary the distance $z_1'$ so as to fulfill the following relation:

$$d1'/d1 \text{ is proportional to } 1x/11$$

This means that it suffices to properly adjust the thickness of the heat compensating plate 14 so that it is gradually smaller from the upper to the lower part, as indicated in FIG. 3. By so doing, the inside of the specimen S and the heat compensating plate 14 which is in contact with it can maintain one and the same temperature all over the surface respectively and, as a result, we can obtain an accuracy of measurement which is much better than the one obtained in that above-mentioned case in which the thickness of the heat compensating plate 14 is constant.

It should be noted that the above example of calculation is based upon the assumption that the temperature gradient in the specimen S is linear and the material (heat conductivity) of the lateral heat insulator 7 and of the heat compensating plate 14 is the same. If there is change in these conditions, then the variation in the thickness of the heat compensating plate 14 will not linear but more complicated.

It should also be noted that although in the above-mentioned first preferred embodiment the gas path 17 which is formed into a double spiral in the heat flow meter 15 with one part almost concentric and the other part bent inward, it may be of course realized in the form of a perfect spiral. In addition, although in the heat flow meter in the above-mentioned case the inlet 18 and outlet 19 for gas are installed on the outer periphery side, they may just as well be installed at the center of the heat flow meter 15 so as to let the measuring gas flow from the center to the outer periphery and then back to the center.

Besides, in the above-mentioned case, although a formed plate of carbon fiber is used as the laminar heat insulator 30a constituting the standard heat transfer plate 30, any other material will do as long as it is has heat-insulating and heat-resistant properties. Besides, as illustrated in FIG. 7, one may just as well form the standard heat transfer plate 30 by winding 2 laminations of two different kinds of materials, one laid on top of the other. If in this case we employ a laminar heat insulator 30a such as, for example, alumina silica paper as one of the two laminas and a highly heat transfer material such as, for example, metal plate 30b as the other lamina, then we can secure a good thermal conductivity in the direction of thickness owing to the metal plate 30b and also obtain the possibility of enlarging the thickness-to-diameter thermal conductivity ratio due to the heat insulator which restricts the thermal conductivity in the radial direction. A combination of graphite heat insulator and graphite foil multi-layer winding proves to be effective for use at high temperatures.

In the above-mentioned case the standard heat transfer plate 30 is provided only on the lower surface of the specimen 30. One may however just as well provide another type of standard heat transfer plate formed in the same way as above on the upper surface of the specimen.

Figure 8:
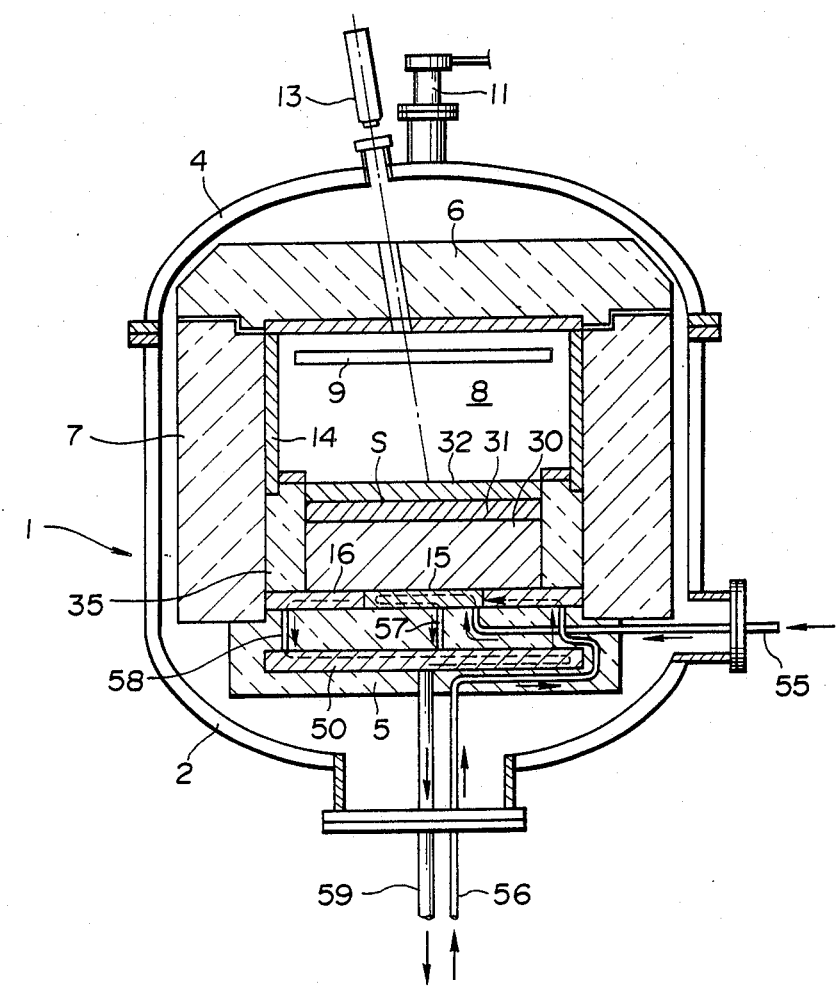
FIG. 8 is a vertical section of the apparatus for measuring thermal conductivity in the second preferred embodiment of the present invention.
Figure 9:
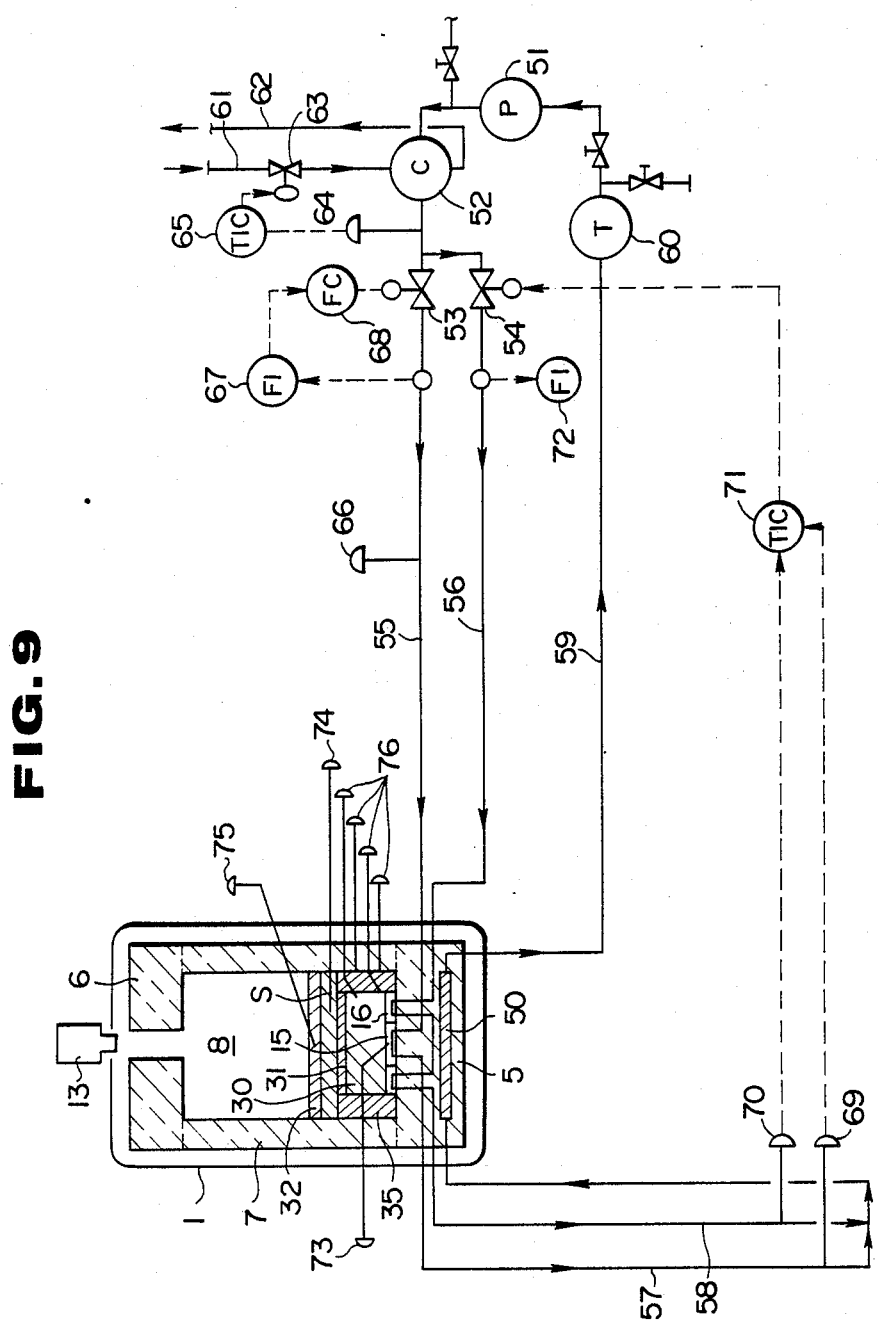
FIG. 9 is a block diagram of the circulating system in the device.

Now, the following explains, by reference to FIGS. 8 to 10, about the second preferred embodiment of the present invention. Here, however, the same constituent elements as those of the device discussed in the above-mentioned first preferred embodiment should be provided with the identical numerals and no detailed explanation is given about them.

The apparatus for measuring thermal conductivity under review in the second preferred embodiment is set up in such a way that the compensating heater 10 referred to in the executed first preferred embodiment is omitted and the heat compensating plate 50 is provided in the lower heat insulator 5. The heat compensating plate 50, like the heat flow meter 15 and the compensating cooling plate 16, contains a path formed into a spiral (not shown) for water which as a heat-measuring fluid is supplied by a circulating system to the heat-measuring plate 15, the compensating cooling plate 16 and the heat compensating plate 50.

This circulating system, which is made up of the main components as illustrated in FIG. 9 including a circulating pump (means for pressurized feed) 51 and a cooler (means for temperature adjustment) 52 installed at the pressure side of the said circulating pump 51, is designed to circulate water for heat transfer by pumping the water with the circulating pump 51 to the cooler 52 where the water is cooled down to a specified temperature before it is led through feed pipes 55 and 56 branched off via flow-control valves 53 and 54 to and then through heat flow meter 15 and the compensating cooling plate 16, as illustrated by arrows and broken lines in FIG. 8, whereupon it passes through communicating tubes 57 and 58 (illustrated as pipe routes in FIG. 9) provided in the lower heat insulator 5 and then through the above-mentioned heat compensating plate 50 and then is pumped through a return pipe 59 and a tank 60 back to the cooler 52.

To the above-mentioned cooler 52 are connected a feed pipe 61 equipped with a flow-control valve 63 for primary cooling water and a return pipe 62. The degree of opening of this flow-control valve 63 is adjusted by the temperature indicator/regulator 65 according to the temperature at the outlet of the cooler 52 thereby making it possible to maintain this temperature at a certain level (for example 50° C.).

The temperature of the water supplied to the heat flow meter 15 through the feed pipe 55 is measured by a thermocouple 66 while the flow rate is regulated by adjustment of the flow-control valve 53. This flow rate is adjusted so that the temperature rise when the water passes through the heat flow meter 15 is a certain value (for example 50° C. or so). Once it is adjusted, the flow rate is maintained constant by the flow-control valve which is automatically controlled by a flow meter 67 and a flow-control gauge 68.

The quantity of the water supplied through the feed pipe 56 to the compensating cooling plate 16 is controlled by the above-mentioned flow-control valve 54 which is adjusted by a temperature indicator/regulator 71 according to the outlet temperature of the heat flow meter 15 and that of the compensating cooling plate 16 measured by thermocouples 69 and 70 so that the said outlet temperatures may be equal to each other while the quantity of flow is indicated by a flow meter 72.

Besides, as illustrated in FIG. 9, the lower surface of the standard heat transfer plate 30, the lower heat-measuring plate 31 and the upper heat-measuring plate 32 are equipped with thermocouples 73, 74 and 75 respectively while the inside and the outside of the heat insulator 35 are equipped with 2 pairs of thermocouples adjacent to each other, i.e. altogether four thermocouples 76, respectively.

To measure the thermal conductivity of the specimen S at a high temperature with the device set up as described above, first place the specimen S in the measuring chamber 8, seal up the measuring chamber 8 with the upper heat insulator 6 and at the same time close the cover 4 of the furnace 1, heat the measuring chamber 8 with the main heater 9 up to a specified preset temperature and maintain the inner temperature of the specimen S at the temperature at which the thermal conductivity is to be measured.

Also, start the circulating pump 51 of the circulating system, maintain the water temperature at the outlet of the cooler 52 constant, for example, at 50° C. and supply water through the feed pipes 55 and 56 to the heat flow meter 15 and the compensating cooling plate 16 of specified flow rates respectively. In the adjustment case, adjust the flow rate of water supplied to the heat flow meter 15, as described above, so as to obtain an increase in the water temperature by 5° C. or so (i.e. so as to obtain an outlet temperature from the heat flow meter 15 of 55° C. or so). At the same time, the water flow rate to the compensating cooling plate 16 is automatically adjusted by the thermocouples 69 and 70, the temperature indicator/regulator 71 and the flow-control valve 54 so that the water temperature at the outlet of the compensating cooling plate 16 is equal to the water temperature at the outlet of the heat flow meter 15 (i.e. 55° C. or so). As a result, the temperature of the heat flow meter 15 and that of the compensating cooling plate are maintained at the same level while water with a temperature of about 55° C. flows into the heat compensating plate 50 from both the heat flow measuring plate 15 and compensating cooling plate 16 thereby causing this heat compensating plate to maintain the said outlet temperature.

When stationary temperature is reached in the measuring chamber 8, the specimen S and the water as heat-measuring fluid, measure the temperature on the upper (front) surface 1 and the lower (back) surface 2 of the specimen S with the thermocouples 75 and 74. Also, accurately measure the temperature of the water flowing through the heat flow meter 15 at the inlet and the outlet with the thermocouples 66 and 69 as well as the flow rate with the flow meter 67 to find the received heat by the heat flow meter 15, i.e. the transmitted heat Q through the specimen S. Also, find the thermal conductivity λ at the set temperature of the specimen S with the above-mentioned equation (1) from the heat flow Q, the upper $\theta_1$ and lower $\theta_2$ surface temperatures of the specimen S and the distance δ from the surface thereof. In this case the effective area A of the specimen S is equal to the area of the heat flow meter 15.

In the apparatus for measuring thermal conductivity of the second preferred embodiment described hitherto, water is used as a circulating fluid and for this reason measuring gas need not be consumed in large quantities nor is there any need for a large amount of heat for preheating the measuring gas so that the running cost can be substantially reduced.

Besides, since in the above-mentioned apparatus for measuring thermal conductivity a fluid with the same temperature as that of the water supplied to the heat flow meter 15 is supplied also to the compensating cooling plate 16, the temperatures of both of the said plates are maintained at a level equal to each other thereby making it possible to eliminate the flow of heat between the said plates, and since the bodies of water which have passed through the plates flow at the same temperature to the heat compensating plate 50, the temperature of the lower heat insulator 5 is maintained at a level slightly higher than that of the said plates so that the flow of heat between the heat flow meter 15 and the lower heat insulator 5 becomes small enough to be neglected. In this apparatus for measuring thermal conductivity, therefore, it is possible to minimize the error of measurement of the amount of heat flow measured by the heat flow meter and hence to further improve the accuracy of measurement of thermal conductivity. As a result, it becomes possible to omit the compensating heater 10 which was necessary in the device illustrated in FIG. 1 and hence to realize the simplification and miniaturization of the device.

In the device according to the second preferred embodiment, on the other hand, a measurement error can be considered due to the heat radiation to the outer part from the heat insulator 35 placed around the specimen S. We can, however, easily correct the measured value and thus further improve the accuracy of measurement by measuring the inside temperature of the insulator 35 with the thermocouples 76 and calculating the amount of heat lost from the heat insulator 35.

Also, in cases, for example, when the above-mentioned compensating plate is not used, the thickness of the lower heat insulator 5 can be made large enough to avoid the risk of a measurement error, and the heat compensating plate 50 may be omitted. If in this case the bodies of water flowing out of the heat flow meter 15 and the compensating cooling plate 16 are made to meet through a duct which in return is made to meander in the lower heat insulator 5, then one can get an equivalent effect as in the case in which the heat compensating plate 50 is provided.

In the device according to the above-mentioned case, the temperature control system is made up of one unit of the cooler 52 and the circulating water is maintained at a constant temperature by controlling the quantity of the primary cooling water supplied to this cooler 52. It is nevertheless quite possible to set up the temperature control system in other ways, for example, as illustrated in FIG. 10. The temperature control system 80 illustrated in FIG. 10, which is made up of a cooler 81 identical with the cooler 52 referred to in the above case and a heating device 83 equipped with a heater 82, should be operated in such a way that the water returning with an elevated temperature (about 55° C. in the example of use according to the above-mentioned case) is excessively cooled to 45° C. or so and then heated up to the specified temperature (50° C.) by the heating device 83. In this case it is not necessary to exactly control the water temperature at the outlet of the cooler 81 (hence the flow-control valve referred to in the above-mentioned case may be omitted), but it suffices to control the water temperature at the outlet of the heater 83 only by controlling the output of the heater 82. Setting up the temperature control system 80 in this way makes it possible to control the circulating water temperature more exactly and more easily.

In addition, for heat-measuring fluid not only just water but also oils or gases may be used. In case a certain gas is used for heat-measuring fluid, then, it suffices to use, for example, a blower in place of the circulating pump and to use flow-control valves and flow meters for gases.

Moreover, although in the above-mentioned case the device is realized as an upright type, it is also quite possible to realize the device as a horizontal type which is set up in such a way that the specimen S is placed in a vertical position in the measuring chamber.

Now, the following explains the third preferred embodiment by reference to FIGS. 11 to 16.

The device according to the third preferred embodiment differs from the one according to the second preferred embodiment in that the standard heat transfer plate 30 is omitted and the specimen S is placed in its position, that found the specimen S is provided a enclosure 100 in place of the heat insulator 35 and that the enclosure 100 and the upper side of the specimen S are covered with a heat transfer plate 101.

The enclosure 100, which is of a cylindrical shape, is arranged in such a way that its lower side makes good contact with the upper side of the compensating cooling plate 16 while its outside makes good contact with the inside of the lateral heat insulator 7. This enclosure 100, as shown in FIG. 12 consists of thin layers of heat insulator 100a made of, for example, formed sheets of carbon fiber densely wound into a spiral of a multi-layer structure. Due to the particular form obtained by winding the thin layer of heat insulator 100a as described above, this enclosure 100 has a thermal conductivity in the axial direction (direction of thickness) substantially (for example about 10 times) larger than that in the radial direction. This means that the enclosure 100 transfers heat easily in the axial direction but with difficulty in the radial direction. Also, the thermal conductivity of the enclosure 100 in the axial direction is substantially (for example about 5 times) larger than that of the above-mentioned lateral heat insulator 7. It is desirable to make the said conductivity in the axial direction substantially larger even than the expected thermal conductivity of the specimen S.

Inside this enclosure 100 is arranged a lower heat-measuring plate 102 with its lower surface making good contact with the upper surface of the heat flow meter 15 and with the compensating cooling plate 16 while on its upper side is placed the specimen S whose thermal conductivity is to be measured and on the upper surface of which is arranged the above-mentioned heat transfer plate 101. This heat transfer plate 101 covers the upper surface of the specimen S and that of the enclosure 100 to maintain the upper surface temperature of the specimen S at the same level as that of the enclosure 100. Also, thermocouples (not shown) for the measurement of the upper and lower temperatures of the specimen S respectively are inserted in the above-mentioned lower heat measuring plate 102 and the heat transfer plate 101.

The heat transfer plate 101, which is illustrated in FIG. 11 as one sheet, may as well be divided into two sections, if necessary, one covering the upper surface of the specimen S and the other one covering that of the enclosure 100.

In the above-mentioned apparatus for measuring thermal conductivity according to the third preferred embodiment the enclosure 100 is arranged inside the measuring chamber 8 while the specimen S is placed inside the said enclosure 100 whose thermal conductivity is substantially larger (i.e. which conducts heat more easily) in the axial direction than in the radial direction so that in this enclosure 100, the heat flow, as illustrated by arrows in FIG. 14 (a), mainly takes place in the axial direction, i.e. downward while the flow in the radial direction, i.e. side way flow, is restricted. Since a heat insulator 7 is provided outside the enclosure, the flow of heat from the enclosure 100 to the heat insulator 7 is restricted by this also suppressing the heat flow in the axial direction.

Also, since the upper surface of the specimen S and of the enclosure 100 is covered with the heat transfer plate 101, both their temperatures are maintained at an equal level. Moreover, since the lower surface of the enclosure 100 is covered with the compensating cooling plate 16 to maintain its lower surface temperature at the same value as that of the specimen S, the inside temperatures of the specimen S and of the enclosure 100 are maintained at almost the same value in the same horizontal section whereby the flow of heat between them can be effectively prevented. A further explanation about this fact will be given in the following by reference to FIG. 14. Let the temperature at the point A on the upper surface and the point B on the lower surface both of the specimen S be $T_1$ and $T_2$ respectively, then the inside temperature of the specimen S will be characterized by a temperature curve X as indicated by a solid line in FIG. 14 (b). The inside temperature curve in such a case is generally extremely similar even among materials of basically different thermal conductivity values. Consequently, in the case when the temperature at point C on the upper surface of the enclosure 100 is $T_1$, i.e. the same as at the point A and the temperature at point D on the lower surface of the enclosure in the same horizontal section as the lower surface of the specimen S is $T_2$, i.e. the same as at point B, then the inside temperature of the enclosure 100 will assume a characteristics as indicated by the temperature curve Y drawn with a dotted line in FIG. 14 (b). These temperature curves X and Y turn out to be almost identical with each others, i.e. both inside temperatures are almost identical with other at any point in the same horizontal section. This fact becomes even more obvious when the thermal conductivity of the enclosure 100 is larger than the expected thermal conductivity of the specimen S. Consequently it is desirable to set the thermal conductivity of the enclosure 100 in the axial direction correspondingly larger.

To prevent the occurrence of an error due to a difference in the relative temperature rise curve of thermal conductivity, it is desirable to prepare several enclosures 100, each made of a material differing in properties from the others, and choose the one similar in properties to the specimen S for use.

It can be seen from the above that the temperatures of the specimen S, the enclosure 100 and the heat insulator 7 present the states of distribution as shown by the isoheats $R_1$ through $R_6$ in FIG. 13 which indicates that the inside temperature of the lateral heat insulator 7 is greatly reduced in the outward direction while there is no temperature difference developed in the same horizontal section of the specimen S and the heat flow compensating cylinder 100. Consequently almost no flow of heat at all takes place between specimen S and the enclosure 100 and the heat inside the specimen S flows exclusively in the direction of thickness and not sideward. As a result, in this apparatus for measuring thermal conductivity, it is possible to substantially improve the accuracy of measurement of the amount of heat flow Q through the heat flow meter 15 and hence the accuracy of measurement of thermal conductivity.

Figure 15:
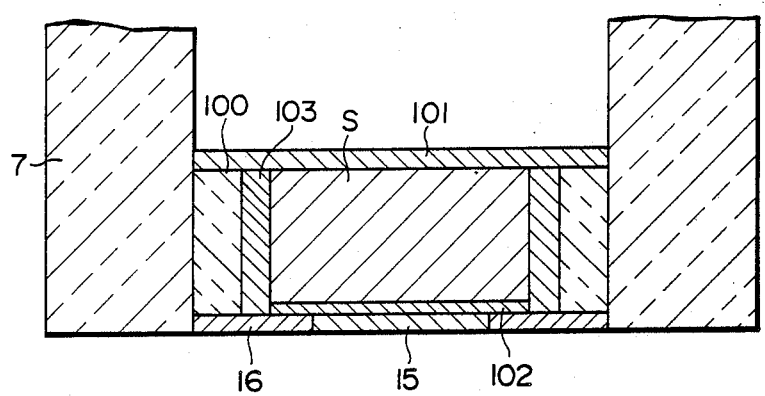
FIG. 15 is a partial vertical section indicating another example of the device.

As illustrated in FIG. 15, one may as well arrange another heat insulator 103 of a cylindrical form inside the enclosure 100. In this case, this heat insulator 103 may be of a normal type or be set up in the same way as the above-mentioned heat-flow-compensating cylinder 100. As can be seen from this, by additionally providing the heat insulator 103 inside the enclosure 100 we can reduce further the influence of an eventual non-negligible difference in the temperature curves X and Y shown in FIG. 14 (b).

Figure 16:
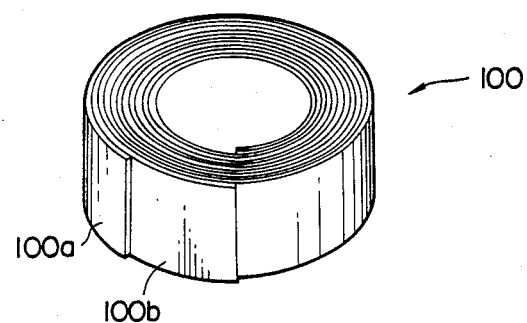
FIG. 16 is a perspective view indicating another example of the heat-flow-compensation cylinder.

Although in the foregoing an example was given in which the enclosure 100 is set up as a spiral made by winding thin strips of the heat insulator 100a with while a formed sheet of carbon fiber employed as the heat insulator 100 a, the configuration of the enclosure is not limited to the type mentioned above only but one may as well employ the enclosure 100 made by winding two thin strips of sheets of different materials one laid on top of the other, as shown in FIG. 16.

If in this case we employ the laminar heat insulator 100a such as, for example, alumina silica paper as one of the two laminas and a highly heat-conductive material such as, for example, a metal plate 100b as the other lamina, then we can not only secure a good thermal conductivity in the direction of thickness owing to the metal plate 100b but also obtain the possibility of enlarging the thickness-to-diameter thermal conductivity ratio due to the heat insulator 100a which suppresses the thermal conductivity in the radial direction. Besides, a combination between graphite heat insulator and graphite foil multi-layer winding proves to be effective for use at high temperatures. Or one may as well form the enclosure using a material with a property such that its thermal conductivity varies according to the direction rather than using the winding of lamina as described above.

Figure 17:
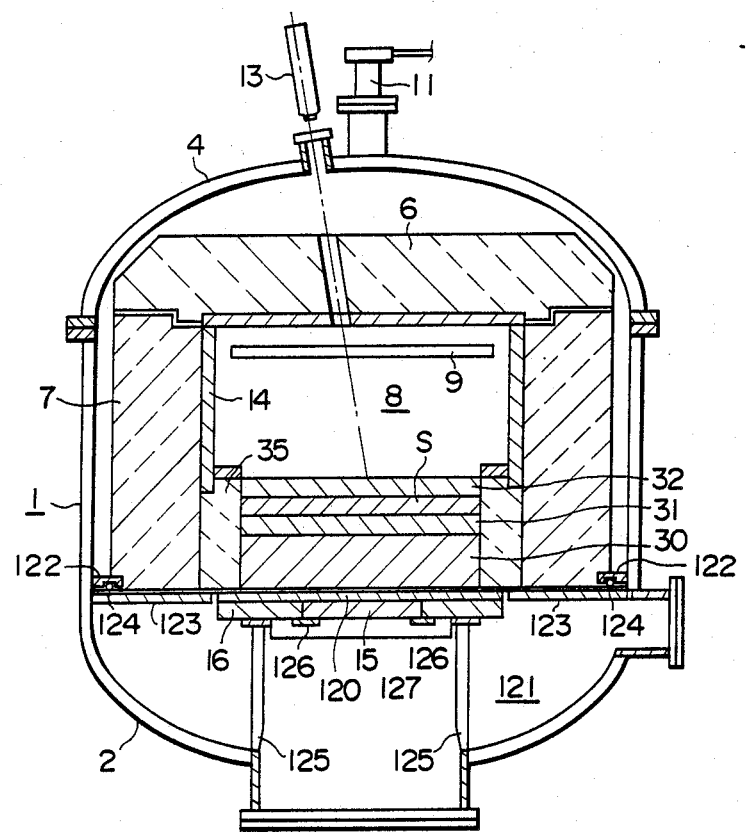
FIG. 17 is a vertical section indicating the fourth preferred embodiment of the apparatus for measuring thermal conductivity of the present invention.

Now, the following explains about the fourth preferred embodiment by reference to FIG. 17.

The device according to the fourth preferred embodiment consists of the second furnace whose inside is divided by a lamina 120 into the measuring chamber 8 in which the specimen S is placed and a vacuum chamber 121 in which a vacuum can be formed.

The lamina 120 which is of a disc shape is installed with its periphery inserted between annular flanges 122 and 123 fixed to the inner surface of the housing 1 while between the flange 122 and the lamina 120 is provided a seal 124 for maintaining a vacuum formed in the vacuum chamber 121. This lamina 120 which is made of a metal plate with an excellent thermal conductivity (for example stainless steel plate) and whose thickness is adequately thin (for example about 0.3 mm) must have an adequate strength to resist the pressure difference between the vacuum chamber 121 and the measuring chamber 8.

On the lower inside of the measuring chamber 8 installed on the upper part of the lamina 120 is arranged a heat insulator 35 of a cylindrical form inside which is arranged the standard heat transfer plate 30 in firm contact with the upper surface of the lamina 120. On the upper surface of the standard heat transfer plate 30 is arranged a lower heat-measuring plate 31 on which is arranged the specimen S whose thermal conductivity is to be measured and on top of which is arranged an upper heat-measuring plate 32.

Inside the vacuum chamber 121 installed on the lower side of the lamina 120 is arranged the disc shaped heat-measuring plate 29 which is attached fast to the lower side of the lamina 120 and at the center of the lower side of which is arranged the heat flow meter 15 around which is located the compensating cooling plate 16 which is supported by a column 125 resting on the bottom of the furnace 1 while the above-mentioned heat-measuring plate 15 is supported by a fixture 126 fixed to the compensating cooling plate 16. On the lower surface of this compensating cooling plate is installed a reflective board 127 which covers the lower side of the heat flow meter 15. The reflective board 127 is made of a metal with an excellent thermal conductivity with its upper surface (surface facing the heat flow meter 15) finished with a mirror surface grade of metallic luster with an extremely small radiation coefficient.

In this device according to the fourth preferred embodiment, the heat radiation can be reduced to an almost negligible degree when conducting measurements with the vacuum chamber 121 kept under vacuum so that an adequate accuracy of measurement can be obtained.

In other words, since in this device the heat flow meter 15 is arranged in the vacuum chamber 121 the heat lost from this heat flow meter 15 to the environment occurs almost exclusively through radiation without a large loss of heat occurring as has been the case until now by heat transfer and convection. Furthermore, the reflective board itself which is arranged on the lower side of the heat flow meter 15 is also intended to reduce radiation heat loss from the compensating cooling plate 16 so that the compensating cooling plate 16 assumes a temperature also equivalent to that of the heat flow meter 15.

A possible heat loss other than the one by radiation is the heat transfer from the heat heat flow meter 15 to the compensating cooling plate 16 through the fixture 126 supporting the heat flow meter 15. The heat flow through the fixture 126, however, can be almost neglected since almost the same temperature is maintained between the heat flow meter 15 and the compensating cooling plate 16.

As for the lamina 120 itself, on the other hand, it may be thought that the heat transfer takes place from the compensating cooling plate 16 to the environment thereby causing a temperature difference between the compensating cooling plate 16 and the heat flow meter 15. The transmitted heat, however, can be almost neglected since the thickness of the lamina 120 is sufficiently small. More specifically, the heat transmitted from the compensating cooling plate 16 to the environment through the lamina 120 is proportional to the area of heat transfer $A_1$ obtained as a product of the length of the periphery of the compensating cooling plate 16 multiplied by the thickness of lamina 120. This area of heat transfer $A_1$ may, if we let the outer dimension of the compensating cooling plate 16 be D and the thickness of the lamina 120 be $\delta$ be expressed as follows:

$$A_1 = \delta \pi D$$

In the meantime the heat transfer area $A_2$ between the lamina 120 on the one hand and the compensating cooling plate 16 and the heat flow meter 15 can be expressed as follows:

$$A_2(\pi/4)D^2$$

Therefore, the ratio the two areas will be:

$$\alpha = A_2/A_1 = D/4d$$

This value $\alpha$ becomes considerably large when the value z is substantially smaller than the value D. For example, when D=50 cm, z=0.03 cm (0.3 mm), then $\alpha$ is equal to about 417. This means that the transmitted heat to the outer periphery through the lamina 120 is of the order of 1/100 of that in the direction of thickness and as such may be said to be nearly negligible. In the meantime, if we always keep the temperature of the compensating cooling plate 16 at the same level as that of the heat flow meter 15 by controlling the temperature or quantity of flow of the heat-measuring fluid supplied to the compensating cooling plate 16, then we can eliminate the influence of the above-mentioned transmitted heat on the accuracy of measurement even if this amount of heat is not negligible.

Meanwhile, in this apparatus for measuring thermal conductivity the vacuum chamber 121 which is evacuated gives rise to the development of a pressure difference between the measuring chamber 8 and the vacuum chamber 121 which is then exerted on the lamina 120. The lamina 120 itself which has an adequate strength, however, is fixed by means of the flanges 122 and 123 at its periphery and is supported by the column 125 through the compensating cooling plate 16.

Meanwhile, due to the pressure difference between the upper and lower sides of the lamina 120, the lamina 120 is pressed fast against the heat-measuring plate 29 while the upper heat-measuring plate 32, the specimen S and the lower heat-measuring plate 31 and the standard heat transfer plate 30 are all pressed fast against the lamina 120, too, so that the development of a gap between them is naturally avoided and hence the heat transfer between them is maintained in a favorable condition. In this respect, too, the accuracy of measurement can be improved.

It should also be noted that the standard heat transfer plate installed on the upper side of the lamina 120 may, if there is no particular need for it, be omitted, thereby causing the lower heat-measuring plate 31 to stick fast to the upper side of the lamina 120.

Also, although in the above-mentioned case an example is given in which a metal plate such as, for example, stainless steel is used for the lamina 120, any other material may as well be used as long as such material can be machined to an adequate thinness and has a good thermal conductivity.

What we claim is:

1. An apparatus for measuring thermal conductivity of a specimen, said specimen defining a first and a second surface and a periphery, said apparatus comprising:
   (a) a measuring chamber adiabatically enclosing an inner space, said measuring chamber containing the specimen and being maintained in contact with the lateral peripheral surface of the specimen to be measured;
   (b) a heat source for uniformly heating the first surface of the specimen;
   (c) a first thermometer to measure the temperature of the first surface of the specimen;
   (d) a heat flow measuring means disposed in contact with the second surface of the specimen in said second space, for maintaining the temperature of the second surface of the specimen at a predetermined temperature and for measuring the thermal energy flowing through the second surface; and
   (e) a second thermometer for measuring the temperature of the second surface of the specimen;
   by which means creating a constant heat flow through the specimen from the first surface of the specimen, through the specimen, and then through the second surface of the specimen, the direction of said constant heat flow defining an axial orientation;
   and measuring the temperature of the first and the second surface of the specimen and thermal energy flowing through the specimen, from which said temperatures and thermal energy the thermal conductivity of the specimen can be determined.

2. An apparatus for measuring thermal conductivity according to claim 1 wherein the measuring chamber has an outer layer with a relatively small thermal conductivity and an inner layer with a relatively large thermal conductivity disposed inside the outer layer, and the specimen is kept in position with its periphery in contact with the inner layer to allow the heat from the heat source to be supplied to the periphery of the specimen through the inner layer, thereby minimizing heat loss from the specimen through its peripheral portion.

3. An apparatus for measuring thermal conductivity according to claim 1 wherein the heat flow measuring device comprises:
   (a) a heat flow meter installed in contact with the second surface of the specimen to maintain the temperature of the second surface at a predetermined temperature and to measure the heat flow through the specimen; and
   (b) a compensating cooling plate installed in contact with the periphery of said heat flow meter to maintain the temperature of the periphery of the specimen at the predetermined temperature and to measure the heat flow through the periphery, whereby suppressing heat loss through the periphery of said heat flow meter.

4. An apparatus for measuring thermal conductivity according to claim 3 wherein the heat flow meter of the heat flow measuring device comprises:
   (a) a first heat flow measuring means having a flow path;
   (b) a first fluid inlet to supply a first fluid of a specified temperature to the flow path and a first fluid outlet to recover the fluid from the flow path of said first heat flow measuring means; and
   (c) first temperature difference measuring means to measure the temperature difference between the supplied first fluid and the recovered first fluid of said first heat flow measuring means;
   the compensating cooling plate comprises:
   (d) a second heat flow measuring means of an annular shape having a flow path therein;
   (e) a second fluid inlet to supply a second fluid of a specified temperature to the flow path and a second fluid outlet to recover the second fluid from the flow path of said second heat flow measuring means; and
   (f) second temperature difference measuring means to measure the temperature difference between the supplied second fluid and the recovered second fluid of said second heat flow measuring means;
   whereby the heat flow through the specimen can be determined according to the temperature difference of the inlets and outlets of said first and the second heat flow measuring means.

5. An apparatus for measuring thermal conductivity according to claim 1 wherein the heat flow measuring device comprises:
   (a) a heat flow measuring means having a flow path therein;
   (b) an inlet to supply a fluid with a specified temperature to the flow path and an outlet to recover the fluid from the flow path; and
   (c) a temperature difference measuring means to measure the temperature difference between the supplied and recovered fluids, whereby the heat flow through the specimen can be determined from the temperature difference of said supplied and recovered fluids.

6. An apparatus for measuring thermal conductivity according to claim 5 wherein the heat flow measuring means comprises a fluid inlet and a fluid outlet formed at an outer peripheral portion thereof and the flow path is formed spirally from the fluid inlet to a central portion of the heat flow meter and from the central portion to the fluid outlet, whereby average temperature of the fluid in adjacent portions of said heat flow meter being approximately equal and the temperature being averaged over the second surface of the specimen.

7. An apparatus for measuring thermal conductivity according to claim 1 wherein the measuring chamber is further enclosed by an outer container.

8. An apparatus for measuring thermal conductivity according to claim 7 wherein said outer container is adapted to maintain a vacuum within so as to suppress heat loss from the measuring chamber and specimen by convection.

9. An apparatus for measuring thermal conductivity of a specimen, said specimen defining a first and a second surface and a periphery, said apparatus comprising:
   (a) measuring chamber adiabatically enclosing an inner space, said measuring chamber containing the specimen and being maintained in contact with the lateral peripheral surface of the specimen to be measured;
   (b) a heat source for uniformly heating the first surface of the specimen;
   (c) a first thermometer to measure the temperature of the first surface of the specimen;
   (d) a reference plate with known conduction characteristics disposed so that a first surface thereof is in contact with a second surface of said specimen;
   (e) a heat flow measuring means disposed in contact with the second surface of the reference plate, for maintaining the temperature of the second surface of the reference plate at a predetermined temperature and for measuring thermal energy flowing through the second surface of said reference plate; and (f) a second thermometer for measuring the temperature of the second surface of the reference plate;

by which means creating a constant heat flow through the first surface of the specimen, through the specimen, through the second surface of the specimen, then through the first surface of the reference plate, through the reference plate, then through the second surface of the reference plate, the direction of said constant heat flow defining an axial orientation;

measuring the temperature of the first surface of the specimen and the second surface of the reference plate, and thermal energy flowing through the specimen and the reference plate, from which said temperatures and thermal energy the thermal conductivity of the specimen can be determined.

10. An apparatus for measuring thermal conductivity according to claim 9 wherein the reference plate comprises an elongated laminar heat transfer element wound spirally from a central portion of the reference plate to a peripheral portion thereof, thereby forming a gap between adjacent windings of the element, whereby the thermal conductivity of the reference plate is smaller in a radial direction than in the axial direction.

11. An apparatus for measuring thermal conductivity according to claim 10 wherein,
(a) the measuring chamber has an outer layer with a relatively small thermal conductivity and an inner layer with a relatively large thermal conductivity disposed inside of the outer layer, and the specimen is kept in position with its periphery in contact with the inner layer to allow the heat from the heat source to be supplied to the periphery of the specimen through the inner layer;
(b) a heat flow meter installed in contact with the second surface of the reference plate to maintain the temperature of the second surface at a predetermined temperature and to measure the heat flow through the reference plate;
(c) a compensating cooling plate installed in contact with the periphery of said heat flow meter to maintain the temperature of the periphery of the reference plate at the predetermined temperature and to measure the heat flow through the periphery, whereby suppressing heat loss through the periphery of said heat flow meter;
(d) a heat flow measuring means having a fluid flow path therein, comprising a fluid inlet and a fluid outlet formed at an outer peripheral portion thereof, and the fluid flow path being formed spirally from the fluid inlet to a central portion of the heat flow meter and from the central portion to the fluid outlet, whereby the average temperature of the fluid in adjacent portions being approximately equal and the temperature being averaged over the second surface of the specimen;
(e) a fluid inlet to supply a fluid with a specified temperature to the flow path and a fluid outlet to recover the fluid from the flow path; and
(f) a temperature difference measuring means to measure the temperature difference between the supplied and recovered fluids, whereby the heat flow through the specimen and the reference plate can be determined from the temperature difference of the fluid.

12. An apparatus for measuring thermal conductivity according to claim 9 wherein the reference plate comprises an elongated laminar heat transfer element formed coaxially creating a gap between adjacent coaxial portions of the element, whereby the thermal conductivity of the reference plate is smaller in a radial direction than in the axial direction.

13. An apparatus for measuring thermal conductivity according to claim 12 wherein,
(a) the measuring chamber has an outer layer with a relatively small thermal conductivity and an inner layer with a relatively large thermal conductivity disposed inside of the outer layer, and the specimen is kept in position with its periphery in contact with the inner layer to allow the heat from the heat source to be supplied to the periphery of the specimen through the inner layer;
(b) a heat flow meter installed in contact with the second surface of the reference plate to maintain the temperature of the second surface at a predetermined temperature and to measure the heat flow through the reference plate;
(c) a compensating cooling plate installed in contact with the periphery of said heat flow meter to maintain the temperature of the periphery of the reference plate at the predetermined temperature and to measure the heat flow loss through the periphery, whereby suppressing heat loss through the periphery of said heat flow meter;
(d) a heat flow measuring means having a fluid flow path therein, comprising a fluid inlet and a fluid outlet formed at an outer peripheral portion thereof, and the fluid flow path being formed spirally from the fluid inlet to a central portion of the heat flow meter and from the central portion to the fluid outlet, whereby the average temperature of the fluid in adjacent portions being approximately equal and the temperature being averaged over the second surface of the specimen;
(e) a fluid inlet to supply a fluid with a specified temperature to the flow path and a fluid outlet to recover the fluid from the flow path; and
(f) a temperature difference measuring means to measure the temperature difference between the supplied and recovered fluids, whereby the heat flow through the specimen and the reference plate can be determined from the temperature difference of the fluid.

14. An apparatus for measuring thermal conductivity according to claim 9 wherein the measuring chamber is further enclosed by an outer container.

15. An apparatus for measuring thermal conductivity of a specimen, said specimen defining a first and second surface and a periphery, said apparatus comprising:
(a) a measuring chamber adiabatically enclosing an inner space, said measuring chamber containing the specimen and being maintained in contact with the lateral peripheral surface of the specimen to be measured;
(b) a heat source for uniformly heating the first surface of the specimen;
(c) a first thermometer to measure the temperature of the first surface of the specimen;
(d) a reference plate with known conduction characteristics disposed so that a first surface thereof is in contact with the second surface of said specimen, said reference plate having relatively less thermal conductivity than the specimen in the axial direction;

(e) a heat flow measuring means disposed in contact with the second surface of the reference plate, for maintaining the temperature of the second surface of the reference plate at a predetermined temperature and for measuring thermal energy flowing through the second surface of said reference plate; and (f) a second thermometer for measuring the temperature of the second surface of the reference plate;

by which means creating a constant heat flow through the specimen and the reference plate from their respective first surfaces and respective second surfaces, a temperature gradient being created in the axial direction, said temperature gradient having the characteristics of a dropping temperature from the first surface of the specimen to the second surface of the reference plate, said dropping temperature demonstrating the largest drop within said reference plate by virtue of said reference plate's relatively less thermal conductivity than the specimen in the axial direction;

and measuring the temperature of the first surface of the specimen and the second surface of the reference plate, and the thermal energy flowing through the specimen and the reference plate, from which said temperatures and thermal energy the thermal conductivity of the specimen can be determined.

* * * * *